United States Patent
Scheuermann (10) Patent No.: US 9,084,883 B2
(45) Date of Patent: Jul. 21, 2015

(54) THIN PROFILE CONDUCTOR ASSEMBLY FOR MEDICAL DEVICE LEADS

(75) Inventor: Torsten Scheuermann, Munich (DE)

(73) Assignee: Cardiac Pacemakers, Inc., St. Paul, MN (US)

(*) Notice: Subject to any disclaimer, the term of this patent is extended or adjusted under 35 U.S.C. 154(b) by 1429 days.

(21) Appl. No.: 12/704,939

(22) Filed: Feb. 12, 2010

(65) Prior Publication Data
US 2010/0234929 A1    Sep. 16, 2010

Related U.S. Application Data (60) Provisional application No. 61/159,572, filed on Mar. 12, 2009.

(51) Int. Cl.
| A61N 1/02 | (2006.01) |
| A61N 1/05 | (2006.01) |
| A61N 1/08 | (2006.01) |

(52) U.S. Cl.
CPC .......... *A61N 1/056* (2013.01); *A61N 2001/086* (2013.01)

(58) Field of Classification Search
CPC .... A61N 2001/086; A61N 1/05; A61N 1/056
USPC .................................................. 607/16, 116
See application file for complete search history.

(56) References Cited

U.S. PATENT DOCUMENTS

| 2,405,449 A | * | 8/1946 | Robinson et al. ............ 428/368 |
| 3,614,692 A | | 10/1971 | Rozelle et al. |
| 4,131,759 A | | 12/1978 | Felkel |
| 4,135,518 A | | 1/1979 | Dutcher |
| 4,146,036 A | | 3/1979 | Dutcher et al. |
| 4,209,019 A | | 6/1980 | Dutcher et al. |
| 4,253,462 A | | 3/1981 | Dutcher et al. |

(Continued)

FOREIGN PATENT DOCUMENTS

| CN | 1762510 A | 4/2006 |
| CN | 1905789 A | 1/2007 |

(Continued)

OTHER PUBLICATIONS

International Search Report and Written Opinion issued in PCT/US2012/055673, mailed Dec. 13, 2012, 10 pages.
International Search Report and Written Opinion issued in PCT/US2009/038629, mailed Jun. 29, 2009, 11 pages.
International Search Report and Written Opinion issued in PCT/US2009/032838, mailed May 4, 2009, 14 pages.

(Continued)

*Primary Examiner* — Christopher D Koharski
*Assistant Examiner* — Jeremiah Kimball
(74) *Attorney, Agent, or Firm* — Faegre Baker Daniels LLP (57) ABSTRACT

A medical device lead includes a thin profile conductor assembly. A proximal connector includes a proximal end that is configured to couple the lead to a pulse generator. An insulative lead body extends distally from the proximal connector. The conductor assembly extends distally from the proximal end within the lead body and includes a non-conductive tubular core member that defines a lumen, an outer insulative layer, and a multilayer conductor between the tubular core member and the outer insulative layer. The multilayer conductor is electrically connected to the proximal connector and includes a first conductive layer adjacent to the tubular core member and a second conductive layer adjacent to the first conductive layer opposite the tubular core member. A conductivity of the second conductive layer is greater than a conductivity of the first conductive layer.

21 Claims, 9 Drawing Sheets

(56) References Cited

U.S. PATENT DOCUMENTS

| | | | |
|---|---|---|---|
| 4,350,169 A | 9/1982 | Dutcher et al. | |
| 4,381,013 A | 4/1983 | Dutcher | |
| 4,404,125 A | 9/1983 | Abolins et al. | |
| 4,437,474 A | 3/1984 | Peers-Trevarton | |
| 4,484,586 A | 11/1984 | McMickle et al. | |
| 4,493,329 A | 1/1985 | Crawford et al. | |
| 4,574,800 A | 3/1986 | Peers-Trevarton | |
| 4,643,202 A | 2/1987 | Roche | |
| 4,649,938 A | 3/1987 | McArthur | |
| 4,869,970 A | 9/1989 | Gulla et al. | |
| 5,002,067 A | 3/1991 | Berthelsen et al. | |
| 5,003,975 A | 4/1991 | Hafelfinger et al. | |
| 5,020,545 A | 6/1991 | Soukup | |
| 5,056,516 A | 10/1991 | Spehr | |
| 5,074,313 A | 12/1991 | Dahl et al. | |
| 5,144,960 A | 9/1992 | Mehra et al. | |
| 5,201,865 A | 4/1993 | Kuehn | |
| 5,217,010 A | 6/1993 | Tsitlik et al. | |
| 5,222,506 A | 6/1993 | Patrick et al. | |
| 5,231,996 A | 8/1993 | Bardy et al. | |
| 5,241,957 A | 9/1993 | Camp et al. | |
| 5,243,911 A | 9/1993 | Dow et al. | |
| 5,246,014 A | 9/1993 | Williams et al. | |
| 5,259,395 A | 11/1993 | Li | |
| 5,300,108 A | 4/1994 | Rebell et al. | |
| 5,324,322 A * | 6/1994 | Grill et al. | 607/118 |
| 5,330,522 A | 7/1994 | Kreyenhagen | |
| 5,354,327 A | 10/1994 | Smits | |
| 5,370,666 A | 12/1994 | Lindberg et al. | |
| 5,378,234 A | 1/1995 | Hammerslag et al. | |
| 5,387,199 A | 2/1995 | Siman et al. | |
| 5,417,208 A * | 5/1995 | Winkler | 600/374 |
| 5,425,755 A | 6/1995 | Doan | |
| 5,456,707 A | 10/1995 | Giele | |
| 5,476,485 A | 12/1995 | Weinberg et al. | |
| 5,483,022 A | 1/1996 | Mar | |
| 5,522,872 A | 6/1996 | Hoff | |
| 5,522,875 A | 6/1996 | Gates et al. | |
| 5,534,018 A | 7/1996 | Wahlstrand et al. | |
| 5,542,173 A | 8/1996 | Mar et al. | |
| 5,545,205 A | 8/1996 | Schulte et al. | |
| 5,549,646 A | 8/1996 | Katz et al. | |
| 5,554,139 A | 9/1996 | Okajima | |
| 5,574,249 A | 11/1996 | Lindsay | |
| 5,584,873 A | 12/1996 | Shoberg et al. | |
| 5,599,576 A | 2/1997 | Opolski | |
| 5,609,622 A | 3/1997 | Soukup et al. | |
| 5,618,208 A | 4/1997 | Crouse et al. | |
| 5,727,552 A | 3/1998 | Ryan | |
| 5,727,553 A | 3/1998 | Saad | |
| 5,728,149 A | 3/1998 | Laske et al. | |
| 5,755,742 A | 5/1998 | Schuelke et al. | |
| 5,760,341 A | 6/1998 | Laske et al. | |
| 5,766,227 A | 6/1998 | Nappholz et al. | |
| 5,800,496 A | 9/1998 | Swoyer et al. | |
| 5,810,887 A | 9/1998 | Accorti, Jr. et al. | |
| 5,817,136 A | 10/1998 | Nappholz et al. | |
| 5,824,026 A * | 10/1998 | Diaz | 607/116 |
| 5,833,715 A | 11/1998 | Vachon et al. | |
| 5,849,031 A | 12/1998 | Martinez et al. | |
| 5,891,114 A | 4/1999 | Chien et al. | |
| 5,891,179 A | 4/1999 | Er et al. | |
| 5,935,159 A | 8/1999 | Cross, Jr. et al. | |
| 5,957,966 A | 9/1999 | Schroeppel et al. | |
| 5,957,970 A | 9/1999 | Shoberg et al. | |
| 5,968,087 A | 10/1999 | Hess et al. | |
| 6,016,447 A | 1/2000 | Juran et al. | |
| 6,057,031 A | 5/2000 | Breme et al. | |
| 6,078,840 A | 6/2000 | Stokes | |
| 6,083,216 A | 7/2000 | Fischer, Sr. | |
| 6,101,417 A | 8/2000 | Vogel et al. | |
| 6,106,522 A | 8/2000 | Fleischman et al. | |
| 6,141,593 A | 10/2000 | Patag | |
| 6,143,013 A | 11/2000 | Samson et al. | |
| 6,178,355 B1 | 1/2001 | Williams et al. | |
| 6,192,280 B1 | 2/2001 | Sommer et al. | |
| 6,208,881 B1 * | 3/2001 | Champeau | 600/374 |
| 6,249,708 B1 | 6/2001 | Nelson et al. | |
| 6,256,541 B1 | 7/2001 | Heil et al. | |
| 6,259,954 B1 | 7/2001 | Conger et al. | |
| 6,289,250 B1 | 9/2001 | Tsuboi et al. | |
| 6,295,476 B1 | 9/2001 | Schaenzer | |
| 6,304,784 B1 * | 10/2001 | Allee et al. | 607/116 |
| 6,317,633 B1 | 11/2001 | Jorgenson et al. | |
| 6,360,129 B1 | 3/2002 | Ley et al. | |
| 6,400,992 B1 | 6/2002 | Borgersen et al. | |
| 6,428,537 B1 * | 8/2002 | Swanson et al. | 606/41 |
| 6,434,430 B2 | 8/2002 | Borgersen et al. | |
| 6,456,888 B1 | 9/2002 | Skinner et al. | |
| 6,493,591 B1 | 12/2002 | Stokes | |
| 6,501,991 B1 | 12/2002 | Honeck et al. | |
| 6,501,994 B1 | 12/2002 | Janke et al. | |
| 6,510,345 B1 | 1/2003 | Van entem | |
| 6,516,230 B2 | 2/2003 | Williams et al. | |
| 6,526,321 B1 | 2/2003 | Spehr | |
| 6,564,107 B1 | 5/2003 | Bodner et al. | |
| 6,671,554 B2 | 12/2003 | Gibson et al. | |
| 6,701,191 B2 * | 3/2004 | Schell | 607/122 |
| 6,721,600 B2 | 4/2004 | Jorgenson et al. | |
| 6,721,604 B1 | 4/2004 | Robinson et al. | |
| 6,813,521 B2 | 11/2004 | Bischoff et al. | |
| 6,850,803 B1 | 2/2005 | Jimenez et al. | |
| 6,854,994 B2 | 2/2005 | Stein et al. | |
| 6,866,044 B2 | 3/2005 | Bardy et al. | |
| 6,906,256 B1 | 6/2005 | Wang | |
| 6,920,361 B2 | 7/2005 | Williams | |
| 6,925,334 B1 | 8/2005 | Salys | |
| 6,944,489 B2 | 9/2005 | Zeijlemaker et al. | |
| 6,949,929 B2 | 9/2005 | Gray et al. | |
| 6,978,185 B2 | 12/2005 | Osypka | |
| 6,985,755 B2 | 1/2006 | Cadieux et al. | |
| 6,985,775 B2 | 1/2006 | Rinke et al. | |
| 6,993,373 B2 | 1/2006 | Vrijheid et al. | |
| 6,999,818 B2 | 2/2006 | Stevenson et al. | |
| 6,999,821 B2 | 2/2006 | Jenney et al. | |
| 7,013,180 B2 | 3/2006 | Villaseca et al. | |
| 7,013,182 B1 | 3/2006 | Krishnan | |
| 7,047,075 B2 | 5/2006 | Stubbs | |
| 7,047,083 B2 | 5/2006 | Gunderson et al. | |
| 7,050,855 B2 | 5/2006 | Zeijlemaker et al. | |
| 7,113,827 B2 | 9/2006 | Silvestri et al. | |
| 7,123,013 B2 | 10/2006 | Gray | |
| 7,127,294 B1 | 10/2006 | Wang et al. | |
| 7,135,978 B2 | 11/2006 | Gisselberg et al. | |
| 7,138,582 B2 | 11/2006 | Lessar et al. | |
| 7,158,837 B2 | 1/2007 | Osypka et al. | |
| 7,174,219 B2 | 2/2007 | Wahlstrand et al. | |
| 7,174,220 B1 | 2/2007 | Chitre et al. | |
| 7,205,768 B2 | 4/2007 | Schulz | |
| 7,239,916 B2 | 7/2007 | Thompson et al. | |
| 7,242,987 B2 | 7/2007 | Holleman et al. | |
| 7,257,449 B2 | 8/2007 | Bodner | |
| 7,289,851 B2 | 10/2007 | Gunderson et al. | |
| 7,363,090 B2 | 4/2008 | Halperin et al. | |
| 7,369,898 B1 | 5/2008 | Kroll et al. | |
| 7,378,931 B2 | 5/2008 | Odahara et al. | |
| 7,388,378 B2 | 6/2008 | Gray et al. | |
| 7,389,148 B1 | 6/2008 | Morgan | |
| 7,453,344 B2 | 11/2008 | Maeda et al. | |
| 7,535,363 B2 | 5/2009 | Gisselberg et al. | |
| 7,571,010 B2 | 8/2009 | Zarembo et al. | |
| 7,610,101 B2 | 10/2009 | Wedan et al. | |
| 7,630,761 B2 | 12/2009 | Salo et al. | |
| 7,689,291 B2 | 3/2010 | Polkinghorne et al. | |
| 7,765,005 B2 | 7/2010 | Stevenson | |
| 7,853,332 B2 | 12/2010 | Olsen et al. | |
| 7,877,150 B2 | 1/2011 | Hoegh et al. | |
| 7,912,552 B2 | 3/2011 | Przybyszewski | |
| 7,917,213 B2 | 3/2011 | Bulkes et al. | |
| 7,933,662 B2 | 4/2011 | Marshall et al. | |
| 7,953,499 B2 | 5/2011 | Knapp et al. | |
| 7,986,999 B2 | 7/2011 | Wedan et al. | |
| 7,991,484 B1 | 8/2011 | Sengupta et al. | |
| 8,000,801 B2 | 8/2011 | Stevenson et al. | |

(56) References Cited

U.S. PATENT DOCUMENTS

| | | |
|---|---|---|
| 8,027,736 B2 | 9/2011 | Wahlstrand et al. |
| 8,032,230 B1 | 10/2011 | Cox et al. |
| 8,046,084 B2 | 10/2011 | Bodner |
| 8,099,177 B2 | 1/2012 | Dahlberg |
| 8,103,360 B2 | 1/2012 | Foster |
| 8,108,054 B2 | 1/2012 | Helland |
| 8,145,324 B1 | 3/2012 | Stevenson et al. |
| 8,170,688 B2 | 5/2012 | Wedan et al. |
| 8,200,342 B2 | 6/2012 | Stevenson et al. |
| 8,214,055 B2 | 7/2012 | Erickson |
| 8,244,346 B2 | 8/2012 | Foster et al. |
| 8,255,055 B2 | 8/2012 | Ameri |
| 8,306,630 B2 | 11/2012 | Stubbs et al. |
| 8,315,715 B2 | 11/2012 | Erickson |
| 8,391,994 B2 | 3/2013 | Foster et al. |
| 8,401,671 B2 | 3/2013 | Wedan et al. |
| 8,543,209 B2 | 9/2013 | Tyers et al. |
| 8,543,218 B2 | 9/2013 | Erickson |
| 8,666,508 B2 | 3/2014 | Foster et al. |
| 8,666,512 B2 | 3/2014 | Walker et al. |
| 8,676,344 B2 | 3/2014 | Desai et al. |
| 2002/0065544 A1 | 5/2002 | Smits |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0028231 A1 | 2/2003 | Partridge et al. |
| 2003/0050680 A1 | 3/2003 | Gibson et al. |
| 2003/0063946 A1 | 4/2003 | Williams et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093136 A1 | 5/2003 | Osypka et al. |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064161 A1 | 4/2004 | Gunderson et al. |
| 2004/0064173 A1 | 4/2004 | Hine et al. |
| 2004/0064174 A1 | 4/2004 | Belden |
| 2004/0088033 A1 | 5/2004 | Smits et al. |
| 2004/0097965 A1 | 5/2004 | Gardeski et al. |
| 2004/0122490 A1 | 6/2004 | Reinke et al. |
| 2004/0153049 A1 | 8/2004 | Hewitt et al. |
| 2004/0162600 A1 | 8/2004 | Williams |
| 2004/0167442 A1 | 8/2004 | Shireman et al. |
| 2004/0172117 A1 | 9/2004 | Hill et al. |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0030322 A1 | 2/2005 | Gardos |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0136385 A1 | 6/2005 | Mann et al. |
| 2005/0177135 A1 | 8/2005 | Hildebrand et al. |
| 2005/0182471 A1 | 8/2005 | Wang |
| 2005/0197677 A1 | 9/2005 | Stevenson |
| 2005/0222642 A1 | 10/2005 | Przbyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0227398 A1* | 10/2005 | Anderson et al. ............. 438/36 |
| 2005/0246007 A1 | 11/2005 | Sommer et al. |
| 2005/0267556 A1 | 12/2005 | Shuros et al. |
| 2005/0272280 A1 | 12/2005 | Osypka |
| 2005/0283167 A1 | 12/2005 | Gray |
| 2006/0009819 A1 | 1/2006 | Przbyszewski |
| 2006/0030774 A1 | 2/2006 | Gray et al. |
| 2006/0037461 A1 | 2/2006 | Yasumura |
| 2006/0041293 A1 | 2/2006 | Mehdizadeh et al. |
| 2006/0041294 A1 | 2/2006 | Gray |
| 2006/0041296 A1 | 2/2006 | Bauer et al. |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0093685 A1 | 5/2006 | Mower et al. |
| 2006/0105066 A1 | 5/2006 | Teague et al. |
| 2006/0106442 A1 | 5/2006 | Richardson et al. |
| 2006/0111768 A1* | 5/2006 | Wessman et al. ............. 607/116 |
| 2006/0118758 A1 | 6/2006 | Wang et al. |
| 2006/0129043 A1* | 6/2006 | Ben-Jacob et al. ........... 600/373 |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0253180 A1 | 11/2006 | Zarembo et al. |
| 2006/0271138 A1 | 11/2006 | MacDonald |
| 2006/0293737 A1 | 12/2006 | Krishman |
| 2007/0010702 A1 | 1/2007 | Wang et al. |
| 2007/0027532 A1 | 2/2007 | Wang et al. |
| 2007/0106332 A1 | 5/2007 | Denker et al. |
| 2007/0112398 A1 | 5/2007 | Stevenson et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1 | 9/2007 | Williams |
| 2007/0255378 A1* | 11/2007 | Polkinghorne et al. ........ 607/119 |
| 2008/0009905 A1 | 1/2008 | Zeijlemaker |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0051854 A1 | 2/2008 | Bulkes et al. |
| 2008/0057784 A1 | 3/2008 | Zarembo et al. |
| 2008/0058902 A1 | 3/2008 | Gray et al. |
| 2008/0119917 A1 | 5/2008 | Geistert |
| 2008/0125754 A1 | 5/2008 | Beer et al. |
| 2008/0129435 A1 | 6/2008 | Gray |
| 2008/0132985 A1 | 6/2008 | Wedan et al. |
| 2008/0132986 A1 | 6/2008 | Gray et al. |
| 2008/0140152 A1* | 6/2008 | Imran et al. ..................... 607/46 |
| 2008/0154348 A1 | 6/2008 | Atalar et al. |
| 2008/0208290 A1 | 8/2008 | Phillips et al. |
| 2008/0243218 A1 | 10/2008 | Bottomley et al. |
| 2008/0262584 A1 | 10/2008 | Bottomley et al. |
| 2008/0269831 A1 | 10/2008 | Erickson |
| 2009/0005825 A1 | 1/2009 | MacDonald |
| 2009/0024180 A1 | 1/2009 | Kisker et al. |
| 2009/0024197 A1 | 1/2009 | Jensen |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1 | 6/2009 | Ameri |
| 2009/0149934 A1 | 6/2009 | Ameri et al. |
| 2009/0198314 A1 | 8/2009 | Foster et al. |
| 2009/0204171 A1 | 8/2009 | Ameri |
| 2009/0210022 A1 | 8/2009 | Powers |
| 2009/0270948 A1 | 10/2009 | Nghiem et al. |
| 2009/0270956 A1 | 10/2009 | Vase et al. |
| 2009/0281608 A1 | 11/2009 | Foster |
| 2010/0010602 A1 | 1/2010 | Wedan et al. |
| 2010/0016935 A1* | 1/2010 | Strandberg et al. ........... 607/116 |
| 2010/0103215 A1 | 4/2010 | Iriguchi |
| 2010/0106215 A1 | 4/2010 | Stubbs et al. |
| 2010/0114277 A1 | 5/2010 | Zhao et al. |
| 2010/0125320 A1 | 5/2010 | Polkinghorne et al. |
| 2010/0137928 A1 | 6/2010 | Duncan et al. |
| 2010/0174348 A1 | 7/2010 | Bulkes et al. |
| 2010/0174349 A1 | 7/2010 | Stevenson et al. |
| 2010/0249892 A1 | 9/2010 | Bulkes et al. |

(56) References Cited

U.S. PATENT DOCUMENTS

| | | |
|---|---|---|
| 2010/0292744 A1 | 11/2010 | Hill et al. |
| 2010/0331936 A1 | 12/2010 | Perrey et al. |
| 2011/0060394 A1 | 3/2011 | Poore |
| 2011/0079423 A1 | 4/2011 | Zhao et al. |
| 2011/0087299 A1 | 4/2011 | Ameri |
| 2011/0087302 A1 | 4/2011 | Ameri |
| 2011/0093054 A1 | 4/2011 | Ameri et al. |
| 2011/0160805 A1 | 6/2011 | Erbstoeszer et al. |
| 2011/0160816 A1 | 6/2011 | Stubbs et al. |
| 2011/0160817 A1 | 6/2011 | Foster et al. |
| 2011/0160818 A1 | 6/2011 | Struve |
| 2011/0160828 A1 | 6/2011 | Foster et al. |
| 2011/0160829 A1 | 6/2011 | Foster et al. |
| 2011/0208280 A1 | 8/2011 | Li et al. |
| 2011/0218422 A1 | 9/2011 | Atalar et al. |
| 2011/0238146 A1 | 9/2011 | Wedan et al. |
| 2011/0288403 A1 | 11/2011 | Kondabatni et al. |
| 2012/0016451 A1 | 1/2012 | Struve et al. |
| 2012/0022356 A1 | 1/2012 | Olsen et al. |
| 2012/0035698 A1 | 2/2012 | Johnson et al. |
| 2012/0053662 A1 | 3/2012 | Foster et al. |
| 2012/0109270 A1 | 5/2012 | Foster |
| 2012/0143273 A1 | 6/2012 | Stubbs et al. |
| 2012/0161901 A1 | 6/2012 | Stevenson et al. |
| 2012/0179233 A1 | 7/2012 | Wedan et al. |
| 2012/0253340 A1 | 10/2012 | Stevenson et al. |
| 2012/0271394 A1 | 10/2012 | Foster et al. |
| 2013/0116764 A1 | 5/2013 | Walker et al. |
| 2013/0158641 A1 | 6/2013 | Foster et al. |
| 2013/0190849 A1 | 7/2013 | Perrey et al. |
| 2013/0190850 A1 | 7/2013 | Wedan et al. |
| 2013/0282093 A1 | 10/2013 | Walker et al. |
| 2013/0325093 A1 | 12/2013 | Foster |
| 2014/0067030 A1 | 3/2014 | Walker et al. |
| 2014/0114383 A1 | 4/2014 | foster et al. |
| 2014/0155972 A1 | 6/2014 | Foster et al. |
| 2014/0324139 A1 | 10/2014 | Foster et al. |

FOREIGN PATENT DOCUMENTS

| | | | |
|---|---|---|---|
| CN | 101039619 A | 9/2007 | |
| EP | 0897997 B1 | 2/1999 | |
| EP | 1594564 A1 | 11/2005 | |
| EP | 1852810 B1 | 11/2007 | |
| JP | 2004141679 A | 5/2004 | |
| JP | 2005501673 A | 1/2005 | |
| JP | 2005515852 A | 6/2005 | |
| JP | 2005515854 A | 6/2005 | |
| WO | WO9606655 A1 | 3/1996 | |
| WO | WO03063953 A2 | 8/2003 | |
| WO | WO 03/089045 | 10/2003 | |
| WO | WO2004073791 A1 | 9/2004 | |
| WO | WO03063946 A2 | 4/2005 | |
| WO | WO2005030322 A1 | 4/2005 | |
| WO | WO2006105066 A2 | 3/2006 | |
| WO | WO2006093685 A1 | 9/2006 | |
| WO | WO 2007/047966 | 4/2007 | |
| WO | WO 2007/089986 | 8/2007 | |
| WO | WO 2007/118194 | 10/2007 | |
| WO | WO-2008/051122 * | 5/2008 | ............... A61N 1/05 |
| WO | WO2008051122 A1 | 5/2008 | |
| WO | WO20090137186 A1 | 11/2009 | |
| WO | WO2010078552 A1 | 7/2010 | |

OTHER PUBLICATIONS

International Search Report and Written Opinion issued in PCT/US2008/085518 on Oct. 29, 2009, 15 pages.
Invitation to Pay Additional Fees and Partial Search Report, dated Aug. 17, 2009, issued in PCT/US2008/085533, 6 pages.
Robert W. Gray, et al., Simple design changes to wires to substantially reduce MRI-induced heating at 1.5T: implications for implanted leads, Magnetic Resonance Imaging, vol. 23, 8, Oct. 2005, pp. 887-891.
International Search Report and Written Opinion issued in PCT/US2010/033686 on Aug. 10, 2010, 12 pages.
International Search Report and Written Opinion issued in PCT/US2010/055130, mailed Mar. 10, 2011, 11 pages.
International Search Report and Written Opinion issued in PCT/US2010/055653, mailed Feb. 1, 2011, 14 pages.
International Search Report and Written Opinion issued in PCT/US2010/024062, mailed Sep. 27, 2010.
Invitation to Pay Additional Fees and Partial Search Report, issued in PCT/US2010/024062, mailed May 7, 2010.
Partial International Search Report issued in PCT/US2013/037432, mailed Jul. 17, 2013, 6 pages.
Partial International Search Report issued in PCT/US2013/013432, mailed Jul. 17, 2013, 6 pages.
"High Voltage Engineering and Testing, 2nd Edition", edited by Hugh M. Ryan, Institution of Engineering and Technology, 2001, 15 pages.
Avalanche Breakdown, Wikipedia Article, captured Apr. 6, 2010, [http://en.wikipedia.org/wiki/Avalanche_breakdown].
Basso, Christophe, "SPICE Model Simulates Spark-Gap Arrestor", Electronics Design, Strategy, and News (EDN), Jul. 3, 1997, 4 pages.
Citel Inc., Data Sheet, BH Series 2 Electrode Miniature Gas Discharge Tube Surge Arrester—8mm, May 14, 2009, 2 pages.
Hayes, David L., Chapter 4, "Generator and Lead Selection" from book entitled "Cardiac Pacing and Defibrillation a Clinical Approach", John Wiley & Sons, (c) 2000 Mayo Foundation, p. 129-157.
International Search Report and Written Opinion issued in PCT/US2009/056843, mailed Dec. 29, 2009, 13 pages.
International Search Report and Written Opinion issued in PCT/US2010/048620, mailed Apr. 5, 2011, 10 pages.
International Search Report and Written Opinion issued in PCT/US2010/053223, mailed Dec. 27, 2010, 11 pages.
International Search Report and Written Opinion issued in PCT/US2011/052541, dated Mar. 9, 2012, 22 pages.
International Search Report and Written Opinion issued in PCT/US2013/057732, mailed Dec. 13, 2013, 11 pages.
Partial International Search Report issued in PCT/US2011/052541, mailed Dec. 6, 2011, 4 pages.
Static Spark Gap Analysis, captured Dec. 24, 2002, [http://www.richieburnett.co.uk/static.html].
International Search Report and Written Opinion issued in PCT/US2013/065517, mailed Dec. 20, 2013, 11 pgs.
File History for U.S. Appl. No. 11/015,807, filed Dec. 17, 2004 to Cooke, Daniel J. et al.
International Search Report and Written Opinion issued in PCT/US2013/037432, mailed Nov. 19, 2013, 17 pages.
Third Party Submission Under 37 CFR 1.290 filed in U.S. Appl. No. 14/056,746 on May 20, 2014, 13 pages.

* cited by examiner

THIN PROFILE CONDUCTOR ASSEMBLY FOR MEDICAL DEVICE LEADS

CROSS-REFERENCE TO RELATED APPLICATION

This application claims priority to Provisional Application No. 61/159,572, filed Mar. 12, 2009, which is herein incorporated by reference in its entirety.

TECHNICAL FIELD

The present invention relates to implantable medical devices. More particularly, the present invention relates to configurations and methods of manufacture for thin profile conductive assemblies for medical device leads.

BACKGROUND

Implantable medical devices for treating a variety of medical conditions with electrical stimuli are well known. Implantable medical devices generally include a medical electrical lead for delivering an electrical stimulus to a targeted site within a patient's body such as, for example, a patient's heart or nervous system. Such leads generally have an elongated, flexible insulating body, one or more inner conductors extending through lumens formed in the body and one or more exposed electrodes connected to the distal ends of the conductors.

Leads may be introduced into the patient's vasculature at a venous access site and transvenously guided through veins to the sites where the lead electrodes will be implanted or otherwise contact tissue at the targeted therapy site. A pulse generator attached to the proximal ends of the conductors delivers an electrical stimulus therapy to the targeted site via the one or more conductors.

SUMMARY

Discussed herein are various conductor assemblies for implantable medical electrical leads including conductive layers having differing electrical conductivities, as well as medical electrical leads including such conductor assemblies.

In Example 1, a medical device lead includes a proximal connector having a proximal end and configured to couple the lead to a pulse generator, an insulative lead body extending distally from the proximal connector, and a conductor assembly extending distally from the proximal end within the lead body. The conductor assembly includes a non-conductive tubular core member that defines a lumen, an outer insulative layer, and a multilayer conductor between the tubular core member and the outer insulative layer. The multilayer conductor is electrically connected to the proximal connector and includes a first conductive layer adjacent the tubular core member and a second conductive layer adjacent the first conductive layer opposite the tubular core member. A conductivity of the second conductive layer is greater than a conductivity of the first conductive layer.

In Example 2, the medical device lead according to Example 1, wherein a thickness of the first conductive layer in a dimension extending between the tubular core member and the outer insulative layer is less than a thickness of the second conductive layer.

In Example 3, the medical device lead according to either Example 1 or 2, wherein the thickness of the first conductive layer is in the range of about 10 to about 30 nm and the thickness of the second conductive layer is in the range of about 0.2 to about 2 μm.

In Example 4, the medical device lead according to any of Examples 1-3, wherein the first conductive layer is comprised of a paramagnetic material and the second conductive layer is comprised of a diamagnetic material.

In Example 5, the medical device lead according to any of Examples 1-4, wherein the first conductive layer is comprised of Ti, and the second conductive layer is comprised of a material selected from the group consisting of Ag, Al, Au, and Pt.

According to Example 6, a method for making a conductive assembly for a medical electrical lead includes masking a non-conductive tubular core member with a pattern. The tubular core member defines a lumen. The method also includes depositing a first conductive layer on the masked tubular core member, and depositing a second conductive layer on the first conductive layer. The second conductive layer has a conductivity greater than the first conductive layer. The method further includes removing the mask from the tubular core member such that portions of the first conductive layer and the second conductive layer deposited on the mask are removed with the mask and a first conductive pattern remains on the tubular core member. The method further includes covering the tubular core member and the first conductive pattern with a first insulative layer.

In Example 7, the method according to Example 6, wherein masking the tubular core member with the pattern comprises spinning a fibrous material over the tubular core member.

In Example 8, the method according to either Example 6 or 7, wherein the first conductive layer is deposited on the masked tube via plasma enhanced chemical vapor deposition (PECVD).

In Example 9, the method according to any of Examples 6-8, wherein the second conductive layer is deposited on the first conductive layer via physical vapor deposition (PVD).

In Example 10, the method according to any of Examples 6-9, wherein the second conductive layer is deposited on the first conductive layer via galvanic deposition.

In Example 11, the method according to any of Examples 6-10, wherein a thickness of the first conductive layer in a dimension extending between the tubular core member and the outer insulative layer is less than a thickness of the second conductive layer.

In Example 12, the method according to any of Examples 6-11, wherein the first conductive layer is comprised of a paramagnetic material and the second conductive layer is comprised of a diamagnetic material.

In Example 13, the method according to any of Examples 6-12, wherein the tubular core member is covered with the first insulative layer via any of spray coating, dip coating, pulsed laser deposition, or condensation.

In Example 14, the method according to any of Examples 6-13, wherein the tubular core member and the first insulative layer are comprised of a polymer.

In Example 15, the method according to any of Examples 6-14, and further comprising (a) masking the first insulative layer with a pattern, (b) depositing a third conductive layer on the masked first insulative layer, (c) depositing a fourth conductive layer on the third conductive layer, wherein the fourth conductive layer has a conductivity greater than the third conductive layer, (d) removing the mask from the first insulative layer such that portions of the third conductive layer and the fourth conductive layer deposited on the mask are removed with the mask and a second conductive pattern remains on the first insulative layer, and (e) covering the first insulative layer and the second conductive pattern with a second insulative layer.

According to Example 16, a conductor assembly for a medical device lead includes a non-conductive tubular core member having a lumen, and an outer insulative layer is disposed about the non-conductive tubular core member. A multilayer conductor is between the tubular core member and the outer insulative layer. The multilayer conductor defines a conductor pattern and includes a first conductive layer adjacent to the tubular core member and a second conductive layer adjacent to the first conductive layer opposite the tubular core member. A conductivity of the second conductive layer is greater than a conductivity of the first conductive layer.

In Example 17, the conductor assembly according to Example 16, wherein a thickness of the first conductive layer in a dimension extending between the tubular core member and the outer insulative layer is less than a thickness of the second conductive layer.

In Example 18, the conductor assembly according to either Example 16 or 17, wherein the thickness of the first conductive layer is in the range of about 10 to about 30 nm and the thickness of the second conductive layer is in the range of about 0.2 to about 2 μm.

In Example 19, the conductor assembly according to any of Examples 16-18, wherein the first conductive layer is comprised of a paramagnetic material and the second conductive layer is comprised of a diamagnetic material.

In Example 20, the conductor assembly according to any of Examples 16-19, wherein the conductor pattern is helical.

In Example 21, the conductor assembly according to any of Examples 16-20, wherein turns of the helical pattern have a varying pitch along a major dimension of the conductor assembly.

In Example 22, the conductor assembly according to any of Examples 16-21, wherein the conductor pattern comprises a plurality of longitudinally extending conductive filars.

In Example 23, the conductor assembly according to any of Examples 16-22, wherein each of the longitudinally extending conductive filars is substantially straight.

In Example 24, the conductor assembly according to any of Examples 16-23, wherein each of the longitudinally extending conductive filars is undulating.

In Example 25, the conductor assembly according to any of Examples 16-24, wherein each of the longitudinally extending conductive filars is serpentine.

In Example 26, the conductor assembly according to any of Examples 16-25, wherein the multilayer conductor defines more than one conductive path.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
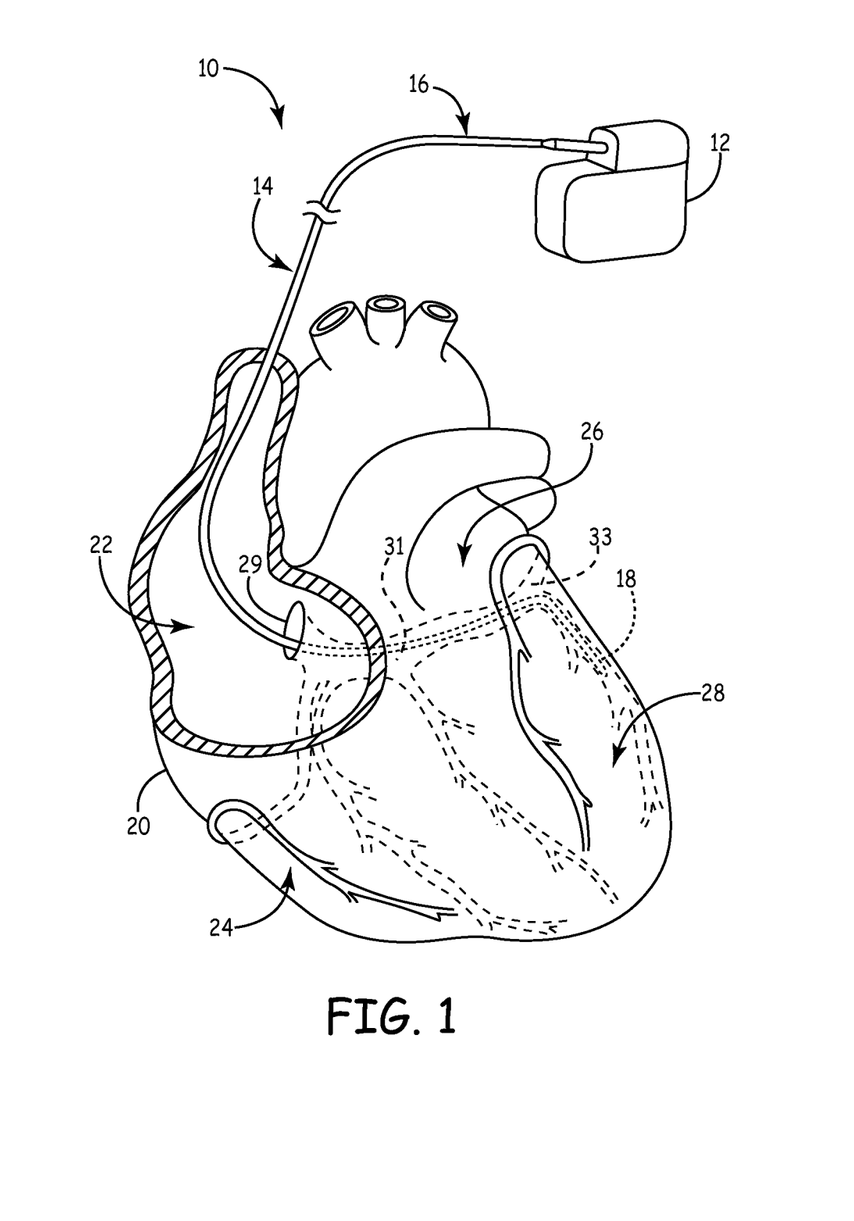
FIG. 1 is a schematic view of a cardiac rhythm management system including a pulse generator coupled to a lead including porous electrodes deployed in a patient's heart.

FIG. 1 is a schematic view of a cardiac rhythm management system 10 including an implantable medical device (IMD) 12 with a lead 14 having a proximal end 16 and a distal end 18. In one embodiment, the IMD 12 includes a pulse generator such as a pacemaker or a defibrillator. The IMD 12 can be implanted subcutaneously within the body, typically at a location such as in the patient's chest or abdomen, although other implantation locations are possible. The proximal end 16 of the lead 14 can be coupled to or formed integrally with the IMD 12. The distal end 18 of the lead 14, in turn, can be implanted at a desired location in or near the heart 20.

As shown in FIG. 1, a distal portion of the lead 14 is disposed in a patient's heart 20, which includes a right atrium 22, a right ventricle 24, a left atrium 26, and a left ventricle 28. In the embodiment illustrated in FIG. 1, the distal end 18 of the lead 14 is transvenously guided through the right atrium 22, through the coronary sinus ostium 29, and into a branch of the coronary sinus 31 or the great cardiac vein 33. The illustrated position of the lead 14 can be used for sensing or for delivering pacing and/or defibrillation energy to the left side of the heart 20, or to treat arrhythmias or other cardiac disorders requiring therapy delivered to the left side of the heart 20.

Additionally, it will be appreciated that the lead 14 can also be used to provide treatment in other regions of the heart 20 (e.g., the right ventricle 24).

Although the illustrative embodiment depicts only a single implanted lead 14, it should be understood that multiple leads can be utilized so as to electrically stimulate other areas of the heart 20. In some embodiments, for example, the distal end of a second lead (not shown) may be implanted in the right atrium 22, and/or the distal end of a third lead (not shown) may be implanted in the right ventricle 24. Other types of leads such as epicardial leads may also be utilized in addition to, or in lieu of, the lead 14 depicted in FIG. 1.

During operation, the lead 14 can be configured to convey electrical signals between the IMD 12 and the heart 20. For example, in those embodiments where the IMD 12 is a pacemaker, the lead 14 can be utilized to deliver electrical stimuli for pacing the heart 20. In those embodiments where the IMD 12 is an implantable cardiac defibrillator, the lead 14 can be utilized to deliver electric shocks to the heart 20 in response to an event such as a heart attack or arrhythmia. In some embodiments, the IMD 12 includes both pacing and defibrillation capabilities.

The electrical signals are carried between the IMD 12 and electrodes at the distal end 18 by one or more conductors extending through the lead 14. The one or more conductors are electrically coupled to a connector suitable for interfacing with the IMD 12 at the proximal end 16 of the lead 14, and to one or more electrodes at the distal end 18. According to the present invention, the one or more conductors have a low profile (i.e., the distance from the center to the outer surface of the lead 14) to minimize the diameter of the lead 14. In addition, the one or more conductors are configured to impart flexibility to the lead 14 to facilitate traversal of tortuous vascular passages during implantation of the lead 14. Also, in some embodiments, the one or more conductors are configured to minimize effects of magnetic resonance imaging (MRI) scans on the functionality and operation of the lead 14. For example, in certain embodiments, the one or more conductors are configured to dissipate electromagnetic energy received by the lead 14 during an MRI scan.

Figure 2:
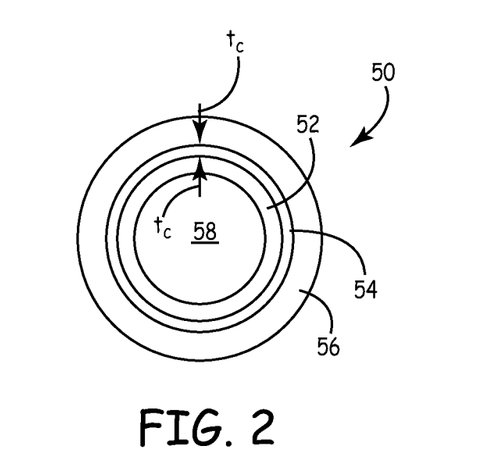
FIG. 2 is a cross-sectional view of a lead shaft assembly including a single conductor layer according to embodiments of the present invention.

FIG. 2 is a cross-sectional view of a lead shaft assembly 50, according to an embodiment of the present invention. The shaft assembly 50 is an exemplary configuration for the body of the lead 14 shown in FIG. 1. The shaft assembly 50 includes an inner core layer 52, an inner conductor 54, and an outer insulative layer 56. The inner conductor 54 is formed on the inner core layer 52, and the outer insulative layer 56 is arranged over the inner conductor 54. A more detailed description of a process for fabricating the shaft assembly 50 will be described in more detail below with regard to FIGS. 7A-7E.

The inner core layer 52 defines a lumen 58 through the shaft assembly 50. In some embodiments, the lumen 58 is sized and shaped to receive a guide wire or stylet employed during implantation of the lead 14. The inner core layer 52 is comprised of a flexible, non-conductive material. In some embodiments, the inner core layer 52 is comprised of a polymeric material, such as polypropylene, polyamide, polyethylene, or polyurethane.

The inner conductor 54 may include one or more layers of conductive material that are deposited onto the inner core layer 52. The conductive material may be deposited using a variety of techniques including, but not limited to, plasma enhanced chemical vapor deposition (PECVD), physical vapor deposition (PVD), or galvanic deposition. The materials used for the inner conductor 54 may be selected to provide good conductivity as well as good adherence to the inner core layer 52. In some embodiments, a thin seed layer is deposited adjacent the inner core layer 52 and a thicker, high conductivity layer is deposited on the seed layer. In some embodiments, the seed layer is comprised of Ti and the high conductivity layer is comprised of Ag, Al, Au, or Pt. In other embodiments, the high conductivity layer is comprised of other materials, such as Nb, Ta, or Ti. The inner conductor 54 has a thickness $t_c$ extending between the inner core layer 52 and the outer insulative layer 56. In some embodiments, the total thickness $t_c$ of the inner conductor 54 is in the range of about 0.2 μm to about 2.0 μm. The thickness $t_c$ for the inner conductor 54 is less than the thickness of conventional lead conductors, providing for a lead with a lower profile and greater flexibility.

The cross-section of the inner conductor 54 may be fabricated to provide a desired impedance at the lead electrode or electrodes to which the inner conductor 54 is attached. In some embodiments, the cross-section of the inner conductor 54 is such that the impedance of each lead electrode is less than about 80Ω. For example, the impedance of each lead electrode may be in the range of about 20Ω to about 80Ω.

The outer insulative layer 56 is arranged over the inner conductor 54 to isolate the inner conductor 54 from the tissue adjacent to the lead 14. The outer insulative layer 56 is made of a flexible, highly durable, fatigue resistant, and bio-compatible insulative material. In some embodiments, the outer insulative layer 56 is comprised of a polymeric material, such as styrene isoprene butadiene (SIBS), polytetrafluoroethylene (PTFE), polyethylene (PE), polypropylene (PP), fluorinated ethylene propylene (FEP), ethylene-tetrafluoroethylene (ETFE), or another biocompatible polymer. In some embodiments, the outer insulative layer 56 is deposited over the inner conductor 54 using processes such as spray coating, dip coating, pulsed laser deposition (PLD), or condensation. The outer insulative layer 56 may alternatively be formed over the combined inner core layer 52 and inner conductor 54 by pulling the assembly through a tube of insulative material.

According to some embodiments, the inner conductor 54 is formed with certain characteristics to provide desired physical, electrical, and/or magnetic properties for the lead 14. For example, the conductive material of the inner conductor 54 may be patterned to minimize the effects of magnetic resonance imaging (MRI) fields on the performance and response of the lead 14. In some embodiments, the inner conductor 54 is patterned to have an inductance that prevents the MRI fields from heating the lead electrodes. In addition, the material or materials for the inner conductor 54 may be selected to provide distortion free imaging by minimizing image artifacts and voids around the lead 14. For example because the magnetization induced in a material when placed in a magnetic field is a function of the magnetic susceptibility of the material, conductive materials having a low magnetic susceptibility (e.g., similar to the magnetic susceptibility of water) may be used. The inner conductor 54 may also be patterned to provide a desired level of flexibility in the lead 14, or to provide increased or decreased flexibility in portions of the lead 14. Furthermore, in embodiments with multiple inner conductors, active electrical elements, such as capacitors and diode AC switches, may be integrated between the conductor paths to avoid coupling of the MRI field into the lead 14.

FIGS. 3-6 are side views of various embodiments of the shaft assembly 50 shown in FIG. 2. Portions of the inner conductor 54 and the outer insulative layer 56 are removed to illustrate each of the layers of the shaft assembly 50. The following embodiments are merely by way of example, and the inner conductor 54 may have any pattern or configuration to provide a lead 14 with desired properties.

Figure 3:
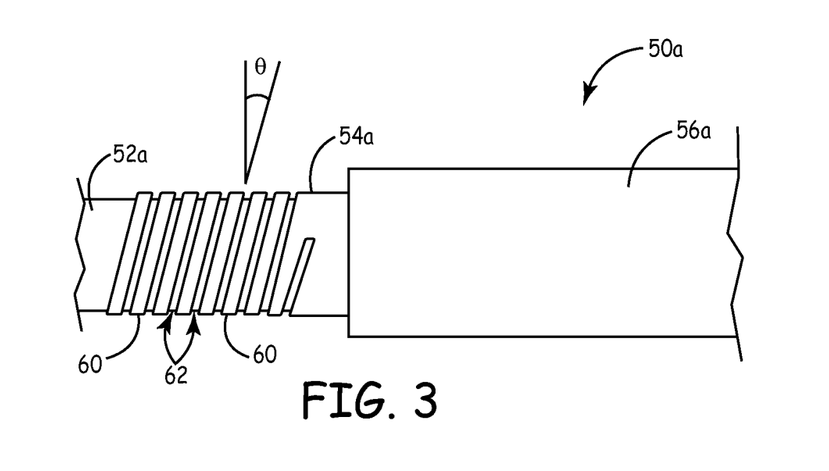
FIG. 3 is a side view of a lead portion including a conductor having a helical pattern, according to an embodiment of the present invention.

FIG. 3 is a side view of a shaft assembly 50a according to an embodiment of the present invention. The shaft assembly 50a includes an inner core layer 52a, an inner conductor 54a, and an outer insulative layer 56a. The inner core layer 52a, inner conductor 54a, and the outer insulative layer 56a may have properties substantially similar to inner core layer 52, inner conductor 54, and outer insulative layer 56, respectively, as described above with regard to FIG. 2. In the embodiment shown in FIG. 3, the inner conductor 54a includes a helical pattern. The helical pattern includes coil members 60 that are separated by spaces 62. The coil members 60 are integral with each other and form a continuous member around the inner core layer 52a. The coil members 60 have a winding angle θ with respect to an axis orthogonal to the major axis of the shaft assembly 50a. In some embodiments, the winding angle θ is in the range of about 1° to about 15°. The winding angle θ, as well as the coil-to-coil width of spaces 62 (i.e., pitch length) and the width of coil members 60, may be controlled to minimize the effect of MRI fields on the inner conductor 54a.

Figure 4:
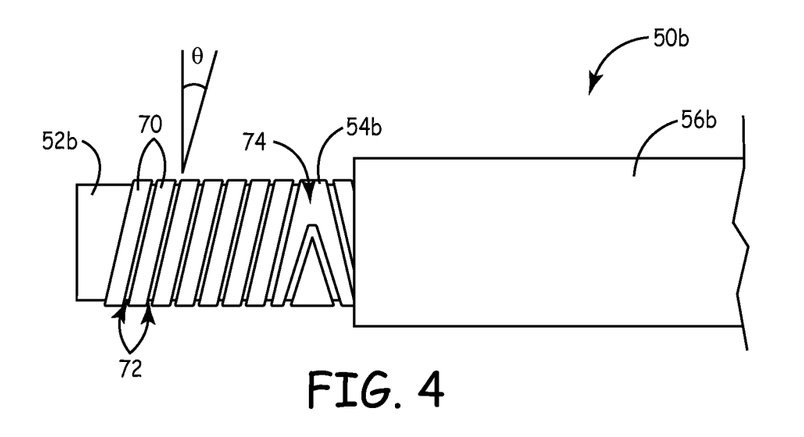
FIG. 4 is a side view of a lead portion including a conductor having a helical pattern with alternating winding directions, according to an embodiment of the present invention.

FIG. 4 is a side view of a shaft assembly 50b according to another embodiment of the present invention. The shaft assembly 50b includes an inner core layer 52b, an inner conductor 54b, and an outer insulative layer 56b. The inner core layer 52b, inner conductor 54b, and the outer insulative layer 56b may have properties substantially similar to inner core layer 52, inner conductor 54, and outer insulative layer 56, respectively, as described above with regard to FIG. 2. In the embodiment shown in FIG. 4, the inner conductor 54b includes a helical pattern having alternating winding directions. The helical pattern includes coil members 70 that are separated by spaces 72. The coil members 70 are integral with each other and form a continuous member around the inner core layer 52b. The direction that the coil members 70 are angled with respect to the inner core layer 52b changes at coil transition section 74. The coil members 70 have a winding angle θ with respect to an axis orthogonal to the major axis of the shaft assembly 50b. In some embodiments, the winding angle of the oppositely directed coil members 70 is substantially the same as the winding angle θ. Alternatively, the winding angle of at least some of the coil members 70 may differ from the winding angle θ. In some embodiments, the winding angle θ is in the range of about 1° to about 15°. The winding angle θ, as well as the pitch length and the width of coil members 70, may be controlled to minimize the effect of MRI fields on the inner conductor 54b.

Figure 5:
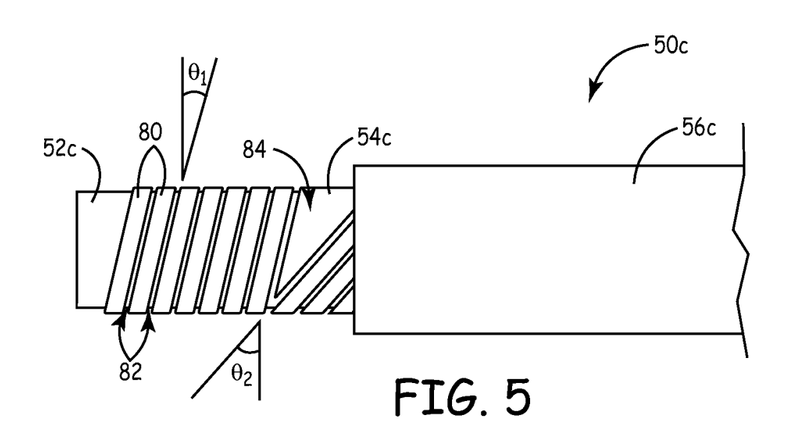
FIG. 5 is a side view of a lead portion including a conductor having a helical pattern with variant winding angles according to an embodiment of the present invention.

FIG. 5 is a side view of a shaft assembly 50c according to another embodiment of the present invention. The shaft assembly 50c includes an inner core layer 52c, an inner conductor 54c, and an outer insulative layer 56c. The inner core layer 52c, inner conductor 54c, and the outer insulative layer 56c may have properties substantially similar to inner core layer 52, inner conductor 54, and outer insulative layer 56, respectively, as described above with regard to FIG. 2. In the embodiment shown in FIG. 5, the inner conductor 54c includes a helical pattern that includes a varying winding angle. The helical pattern includes coil members 80 that are separated by spaces 82. The coil members 80 are integral with each other and form a continuous member around the inner core layer 52c. The angle at which the coil members 80 are disposed with respect to the inner core layer 52c changes at coil transition section 84. The coil members 80 have a first winding angle $θ_1$ with respect to an axis orthogonal to the major axis of the shaft assembly 50c along a first portion of the shaft assembly 50c, and a second winding angle $θ_2$ with respect to an axis orthogonal to the major axis of the shaft assembly 50c along a second portion of the shaft assembly 50c. In some embodiments, the first winding angle $θ_1$ is in the range of about 1° to about 15°, and the second winding angle $θ_2$ is in the range of about 15° to about 60°. The winding angles $θ_1$ and $θ_2$, as well as the pitch length and the width of coil members 80, may be controlled to minimize the effect of MRI fields on the inner conductor 54c.

Figure 6:
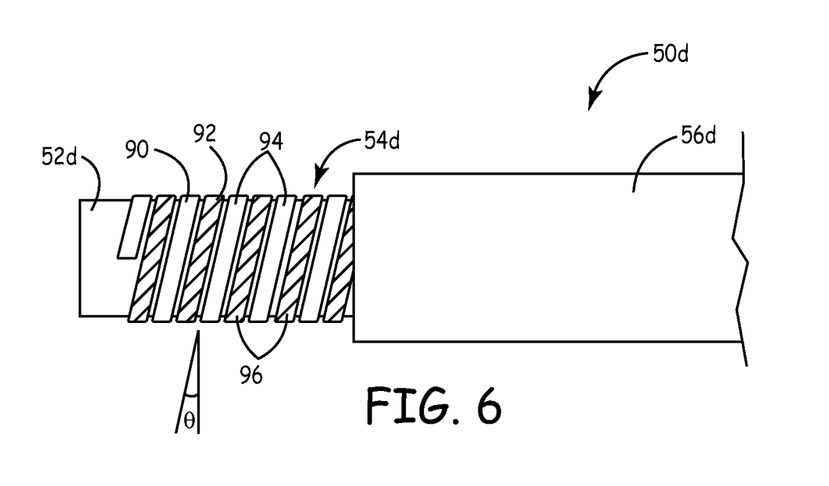
FIG. 6 is a side view of a lead portion including a conductor having multiple filars in a helical pattern, according to an embodiment of the present invention.

FIG. 6 is a side view of a shaft assembly 50d according to another embodiment of the present invention. The shaft assembly 50d includes an inner core layer 52d, an inner conductor 54d, and an outer insulative layer 56d. The inner core layer 52d, inner conductor 54d, and the outer insulative layer 56d may have properties substantially similar to inner core layer 52, inner conductor 54, and outer insulative layer 56, respectively, as described above with regard to FIG. 2. In the embodiment shown in FIG. 6, the inner conductor 54d includes two co-radial conductive filars 90 and 92 that include a helical pattern. The helical pattern of conductive filar 90 includes coil members 94, and the conductive filar 92 includes coil members 96. The coil members 94 are integral with each other and form a continuous member around the inner core layer 52d. Likewise, the coil members 96 are integral with each other and form a continuous member around the inner core layer 52d. The coil members 94 and 96 each have a winding angle θ with respect to an axis orthogonal to the major axis of the shaft assembly 50d. In some embodiments, the winding angle θ is in the range of about 1° to about 15°. The winding angle θ as well as the spacing between the filars 90 and 92 and the width of coil members 94 and 96, may be controlled to minimize the effect of MRI fields on the inner conductor 54d.

Figure 7A:
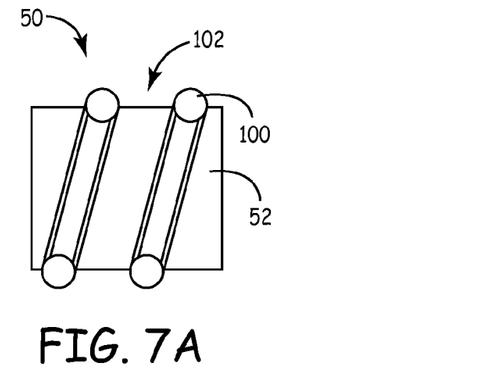
FIGS. 7A-7E illustrate steps in fabricating a conductor with a helical pattern according to the present invention.

FIGS. 7A-7E illustrate steps in an embodiment of a process for fabricating the shaft assembly 50. The process illustrated in FIGS. 7A-7E may be employed to fabricate any of the shaft assemblies 50a-50d illustrated in FIGS. 3-6. In FIG. 7A, a first step of the process is shown, wherein a portion of the inner core layer 52 is shown masked with a pattern. The inner core layer 52 may be masked with a pattern that is related to the desired pattern that the conductive layer 54 will have. In the embodiment shown, a fiber 100 is wound or spun over the inner core layer 52. For example, the inner core layer 52 may be rotated, and the fiber 100 subsequently wrapped around the rotating inner core layer 52. In some embodiments, the fiber 100 is a metal fiber. The fiber 100 is wound or spun onto the inner core layer 52 tight enough to impress into the surface 102 of the inner core layer 52, as is shown in FIG. 7A. In embodiments in which the conductive layer 54 deposited on the inner core layer 52 is not patterned (i.e., the conductive layer 54 is a solid member), then this step may be omitted.

Figure 7B:
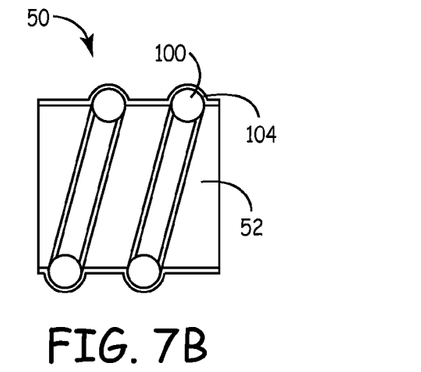

FIG. 7B is a side view of a second step of a process for fabricating the shaft assembly 50, in which the combined inner core layer 52 and fiber 100 is base coated with a base layer 104. The seed layer 104 is comprised of a material that adheres well to the material of the inner core layer 52. In some embodiments, the material is conductive and paramagnetic. One example material that may be deposited as the base layer 104 is titanium. In some embodiments, the base layer 104 has a thickness in the range of about 10 nm to about 30 nm. The base layer 104 may be deposited onto the shaft assembly 50 using a variety of techniques including, for example, plasma enhanced chemical vapor deposition (PECVD). This technique is described in European Patent No. 0897997, entitled "Composite Material," which is hereby incorporated by reference in its entirety.

Figure 7C:
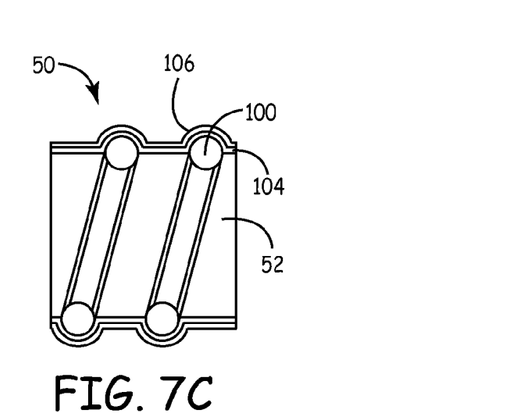

FIG. 7C is a side view of a third step of a process for fabricating the shaft assembly 50, in which a conductive layer 106 of material is deposited onto the base layer 104. In the embodiment shown, the combined base layer 104 and conductive layer 106 form the inner conductor 54 as described above with regard to FIG. 2. The conductive layer 106 has a conductivity that is greater than the conductivity of the base layer 104. In addition, the conductive layer 106 may be diamagnetic. Example materials that may be used for the conductive layer 106 include, for example, gold or copper. The conductive layer 106 may have a thickness that is greater than the thickness of the base layer 104. In some embodiments, the thickness of the conductive layer 106 is in the range of about 0.2 µm to about 2.0 µm. For ease of illustration, this substantial difference in thickness is not illustrated in FIG. 7C. The use of a larger volume of a diamagnetic material, which has negative magnetic susceptibility, with a very small volume of paramagnetic material results in substantially distortion free imaging, with minimal image artifacts or voids around the lead in the magnetic resonance image. In addition, if gold is used for the conductive layer 106, good x-ray contrasting is provided.

The conductive layer 106 may be deposited onto the base layer 104 in a variety of ways. In some embodiments, the conductive layer 106 is deposited via physical vapor deposition (PVD). In other embodiments, the conductive layer 106 is deposited via galvanic deposition. In further embodiments, the conductive layer 106 is deposited by sputtering, such as laser sputtering. In still further embodiments, the conductive layer 106 is deposited using other techniques suitable for coating the base layer 104 with the conductive layer 106.

Figure 7D:
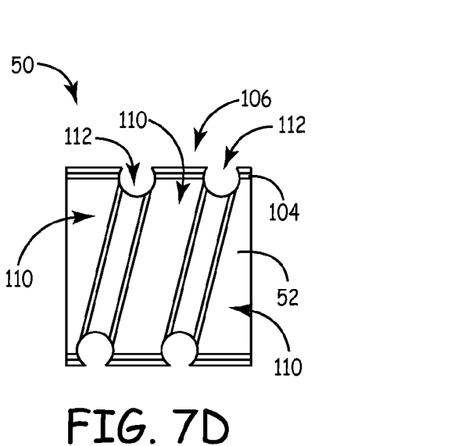

FIG. 7D is a side view of a fourth step of a process for fabricating the shaft assembly 50, in which the mask (i.e., fiber 100) is removed from the inner core layer 52. When the fiber 100 is removed from the inner core layer 52, the portions of the base layer 104 and the conductive layer 106 that were on the fiber 100 are also removed. As a result, coil members 110 remain on the inner core layer 52, and the portions of the assembly from which the fiber 100 was removed define spaces 112 between the coil members 110. In the embodiment shown, the spaces 112 are indented relative to the outer surface 102 (FIG. 7A) due to the tight winding of the fiber 100. In the step shown in FIG. 7D, the inner core layer 52 is exposed in the spaces 112. In an alternative embodiment, the fiber 100 does not indent the outer surface 102 of the inner core layer 52.

Figure 7E:
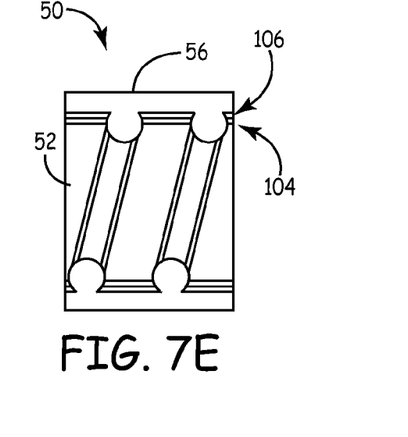

FIG. 7E is a side view of a fifth step of a process for fabricating the shaft assembly 50, in which the outer insulative layer 56 is arranged over the conductive layer 106. The outer insulative layer 56 coats the outside of the shaft assembly 50 and fills the spaces 112 between the coil members 110 with the insulative material to isolate adjacent coil turns from each other. In some embodiments, the outer insulative layer 56 is deposited over the conductive layer 106 using processes such as spray coating, dip coating, pulsed laser deposition (PLD), or condensation. The outer insulative layer 56 may alternatively be formed over the combined inner core layer 52 and inner conductor 54 by pulling the assembly through a tube of insulative material.

Figure 8:
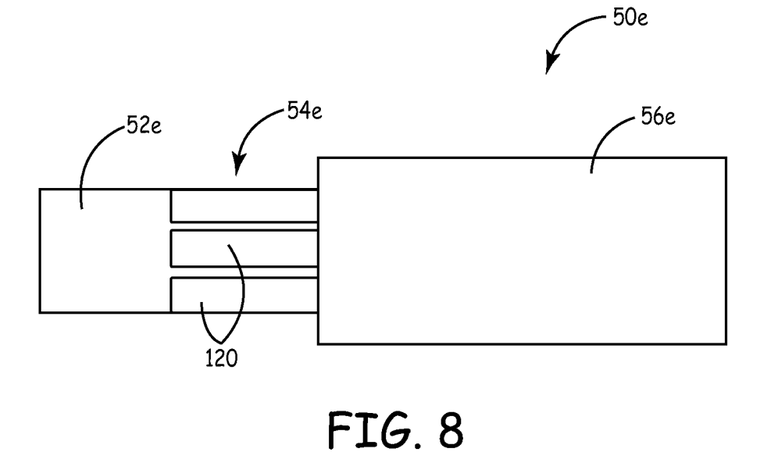
FIG. 8 is a side view of a lead portion including a conductor having a plurality of parallel longitudinally extending straight filars, according to an embodiment of the present invention.

It will be appreciated that the configuration for the inner conductor 54 is not limited to the helical pattern shown, and that the principles of the present invention may be applied to inner conductors 54 having other types of patterns. For example, FIG. 8 is a side view of a shaft assembly 50e including an inner core layer 52e, an inner conductor 54e, and an outer insulative layer 56e. The inner core layer 52e, inner conductor 54e, and the outer insulative layer 56e may have properties substantially similar to inner core layer 52, inner conductor 54, and outer insulative layer 56, respectively, as described above with regard to FIG. 2. In the embodiment shown in FIG. 8, the inner conductor 54e includes a plurality of parallel longitudinally extending straight filars 120. In some embodiments, the filars 120 are connected to the same contact at the IMD 12 to carry a signal between the IMD 12 and the heart 20. In other embodiments, each of the filars 120 is employed to carry a separate signal between the IMD 12 and the heart 20.

Figure 9:
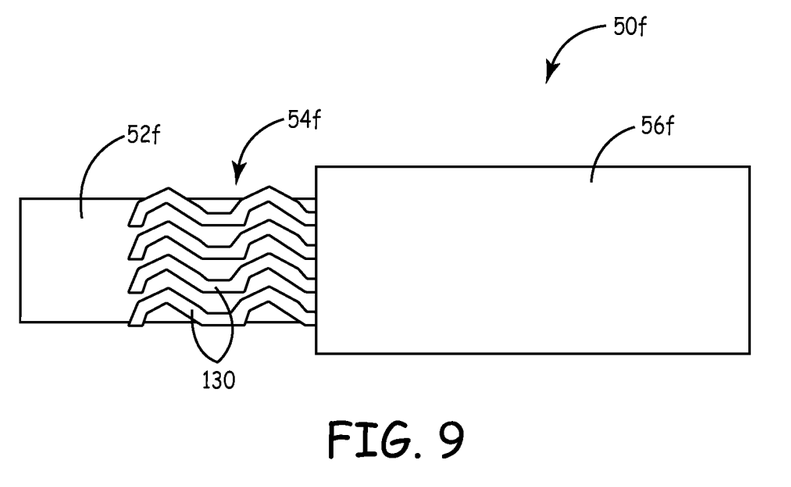
FIG. 9 is a side view of a lead portion including a conductor having a plurality of parallel longitudinally extending undulating filars, according to an embodiment of the present invention.

FIG. 9 is a side view of a shaft assembly 50f including an inner core layer 52f, an inner conductor 54f, and an outer insulative layer 56f. The inner core layer 52f, inner conductor 54f, and the outer insulative layer 56f may have properties substantially similar to inner core layer 52, inner conductor 54, and outer insulative layer 56, respectively, as described above with regard to FIG. 2. In the embodiment shown in FIG. 9, the inner conductor 54f includes a plurality of parallel longitudinally extending undulating filars 130. In some embodiments, the filars 130 are connected to the same contact at the IMD 12 to carry an electrical signal between the IMD 12 and the heart 20. In other embodiments, each of the filars 130 is employed to carry a separate electrical signal between the IMD 12 and the heart 20.

Figure 10:
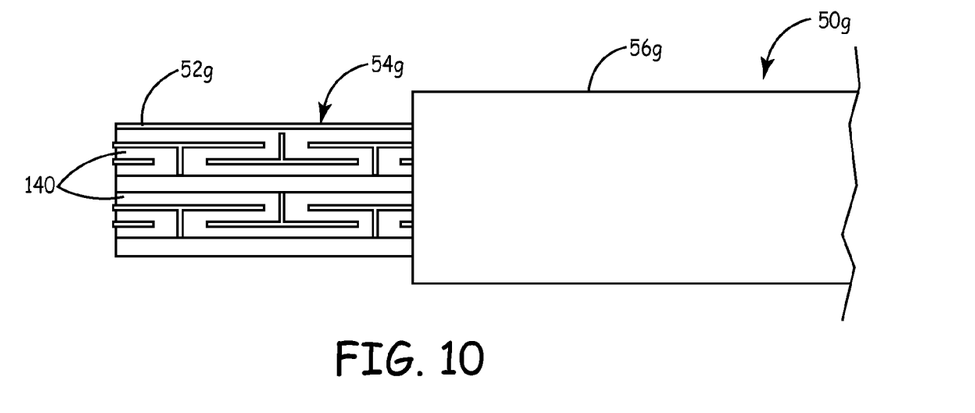
FIG. 10 is a side view of a lead portion including a conductor having a plurality of parallel longitudinally extending serpentine filars, according to an embodiment of the present invention.

FIG. 10 is a side view of a shaft assembly 50g including an inner core layer 52g, an inner conductor 54g, and an outer insulative layer 56g. The inner core layer 52g, inner conductor 54g, and the outer insulative layer 56g may have properties substantially similar to inner core layer 52, inner conductor 54, and outer insulative layer 56, respectively, as described above with regard to FIG. 2. In the embodiment shown in FIG. 10, the inner conductor 54g includes a plurality of parallel longitudinally extending serpentine filars 140. In some embodiments, the filars 140 are connected to the same contact at the IMD 12 to carry an electrical signal between the IMD 12 and the heart 20. In other embodiments, each of the filars 140 is employed to carry a separate electrical signal between the IMD 12 and the heart 20.

Figure 11:
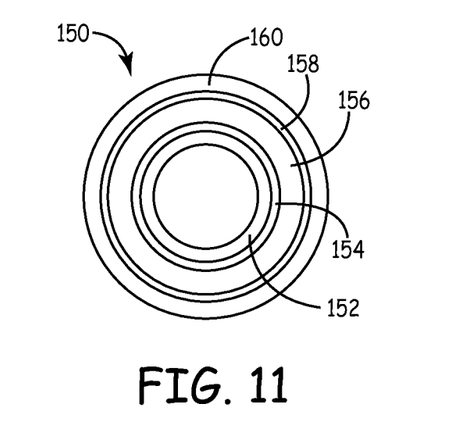
FIG. 11 is a cross-sectional view of a lead shaft assembly including a multiple conductor layers according to embodiments of the present invention.

In certain applications, the lead 14 (FIG. 1) may include multiple co-axial conductors to carry signals having different purposes or electrical characteristics between the IMD 12 and the heart 20. For example, FIG. 11 is a cross sectional view of a shaft assembly 150 including an inner core layer 152, a first inner conductor 154, an intermediate insulative layer 156, a second inner conductor 158, and an outer insulative layer 160. The first inner conductor 154 is formed on the inner core layer 152, the intermediate insulative layer 156 is formed on the first inner conductor 154, the second inner conductor 158 is formed on the intermediate insulative layer 156, and the outer insulative layer 160 is arranged over the inner conductor 158. The inner core layer 152 may have properties substantially similar to the inner core layer 52, the inner conductors 154 and 158 may have properties substantially similar to the inner conductor 54, and the intermediate insulative layer 156 and the outer insulative layer 160 may have properties substantially similar to the outer insulative layer 56. In addition, the layers of the shaft assembly 150 may be formed using techniques substantially similar to those described above with regard to FIGS. 7A-7E.

Figure 12:
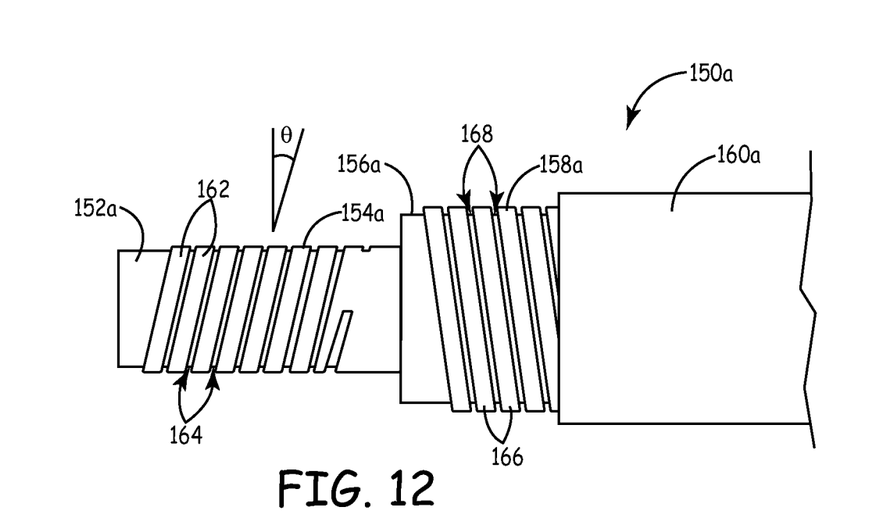
FIG. 12 is a side view of a lead portion including multiple conductors having a helical pattern, according to an embodiment of the present invention.

FIG. 12 is a side view of a shaft assembly 150a according to an embodiment of the present invention. The shaft assembly 150a includes an inner core layer 152a, a first inner conductor 154a, an intermediate insulative layer 156a, a second inner conductor 158a, and an outer insulative layer 160a. In the embodiment shown in FIG. 12, the inner conductors 154a and 158a each includes a helical pattern. The helical pattern of the first inner conductor 154a includes coil members 162 that are separated by spaces 164, and the helical pattern of the second inner conductor 158a includes coil members 166 that are separated by spaces 168. The coil members 162 and 166 are oppositely oriented with respect to an axis orthogonal to the major axis of the shaft assembly 150a. The coil members 162 have a winding angle θ that, in some embodiments, is in the range of about 1° to about 15°. In the embodiment shown, the winding angle of the oppositely directed coil members 166 of the second inner conductor 158a is substantially the same as the winding angle θ. In alternative embodiments, the winding angle of the oppositely directed coil members 166 is different than the winding angle θ.

Figure 13:
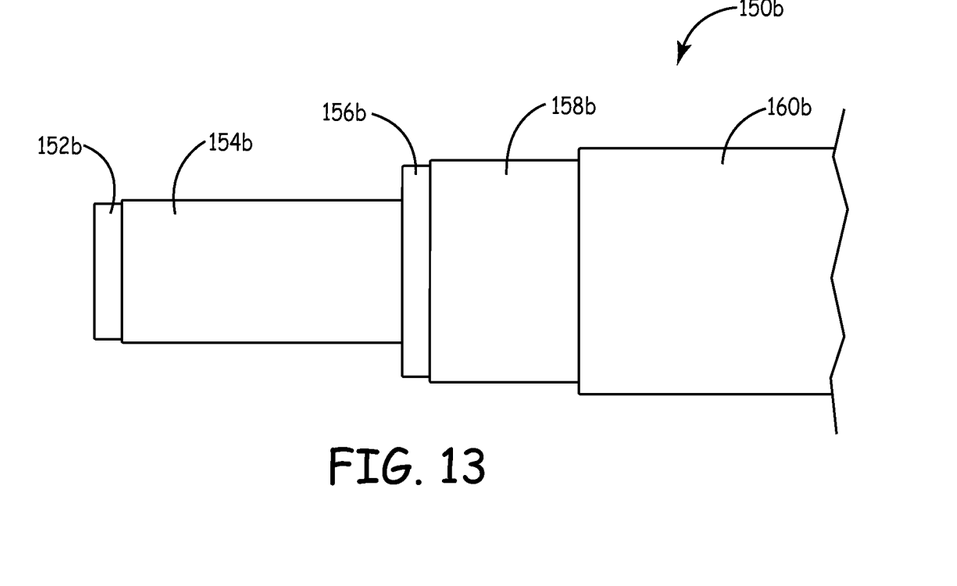
FIG. 13 is a side view of a lead portion including multiple solid conductors, according to an embodiment of the present invention.

FIG. 13 is a side view of a shaft assembly 150b according to an embodiment of the present invention. The shaft assembly 150b includes an inner core layer 152b, a first inner conductor 154b, an intermediate insulative layer 156b, a second inner conductor 158b, and an outer insulative layer 160b. In the embodiment shown in FIG. 12, the inner conductors 154a and 158a are a solid layer of conductive material.

It will be appreciated that while two inner conductors 154 and 158 are shown in the embodiments of FIGS. 12 and 13, any number of inner conductors may be included in the shaft assembly 150 by patterning additional layers of conductive material on the outside of the shaft assembly, separated by layers of insulative material. In addition, it will be appreciated that the inner conductors 154 and 158 may be fabricated into any pattern including, for example, those described above in FIGS. 3-6 and FIGS. 8-10.

In summary, the present invention relates to a medical device lead including a thin profile conductor assembly. A proximal connector includes a proximal end that is configured to couple the lead to a pulse generator. An insulative lead body extends distally from the proximal connector. The conductor assembly extends distally from the proximal end within the lead body and includes a non-conductive tubular core member that defines a lumen, an outer insulative layer, and a multilayer conductor between the tubular core member and the outer insulative layer. The multilayer conductor is electrically connected to the proximal connector and includes a first conductive layer adjacent to the tubular core member and a second conductive layer adjacent to the first conductive layer opposite the tubular core member. A conductivity of the second conductive layer is greater than a conductivity of the first conductive layer. A medical device lead conductor as described has a very low profile, providing leads having small diameters. In addition, the conductor is configured to impart increased flexibility to the lead to facilitate traversal of tortuous vascular passages during implantation of the lead. The conductor may also include features or configurations that make the lead suitable for magnetic resonance imaging (MRI) environments.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof. For example, while the deposited conductive material has been described with regard to the inner conductor(s) of a cardiac lead it will be appreciated that the principles of the present invention are applicable to other types of leads, such as neuromodulation leads, as well as other types of conductive coating applications, such as housings, flexible electrodes, and electromagnetic interference (EMI) shielding.

I claim:

1. A method for making a conductive assembly for a medical electrical lead, the method comprising:
    masking a non-conductive tubular core member by winding a mask helically around the non-conductive tubular core member to form gaps between adjacent turns of the mask, wherein the tubular core member defines a lumen;
    depositing a first conductive layer on the masked tubular core member, the first conductive layer deposited on the non-conductive tubular core member in the gaps between adjacent turns of the mask;
    depositing a second conductive layer on the first conductive layer, wherein the second conductive layer has a conductivity greater than the first conductive layer;
    removing the mask from the tubular core member such that portions of the first conductive layer and the second conductive layer deposited on the mask are removed with the mask and a helical conductive pattern remains on the tubular core member, the helical conductive pattern comprising the first conductive layer and the second conductive layer; and
    covering the tubular core member and the helical conductive pattern with a first insulative layer.

2. The method of claim 1, wherein masking the tubular core member comprises spinning a fibrous material over the tubular core member.

3. The method of claim 1, wherein the first conductive layer is deposited on the masked tube via plasma enhanced chemical vapor deposition (PECVD).

4. The method of claim 1, wherein the second conductive layer is deposited on the first conductive layer via physical vapor deposition (PVD).

5. The method of claim 1, wherein the second conductive layer is deposited on the first conductive layer via galvanic deposition.

6. The method of claim 1, wherein a thickness of the first conductive layer in a dimension extending between the tubular core member and the outer insulative layer is less than a thickness of the second conductive layer.

7. The method of claim 1, wherein the first conductive layer is comprised of a paramagnetic material and the second conductive layer is comprised of a diamagnetic material.

8. The method of claim 1, wherein the tubular core member is covered with the first insulative layer via any of spray coating, dip coating, pulsed laser deposition, or condensation.

9. The method of claim 1, wherein the tubular core member and the first insulative layer are comprised of a polymer.

10. The method of claim 1, and further comprising:
    masking the first insulative layer with a pattern;
    depositing a third conductive layer on the masked first insulative layer;
    depositing a fourth conductive layer on the third conductive layer, wherein the fourth conductive layer has a conductivity greater than the third conductive layer;
    removing the mask from the first insulative layer such that portions of the third conductive layer and the fourth conductive layer deposited on the mask are removed with the mask and a second conductive pattern remains on the first insulative layer; and
    covering the first insulative layer and the second conductive pattern with a second insulative layer.

11. The method of claim 1, wherein masking the non-conductive tubular core member further comprises indenting the non-conductive tubular core member with the mask as the mask is helically wound around the non-conductive tubular core member.

12. The method of claim 1, wherein removal of the mask from around the tubular core member exposes spaces of the non-conductive tubular core member between adjacent turns of the helical conductor pattern.

13. The method of claim 12, wherein covering the tubular core member with the first insulative layer comprises filling the spaces between adjacent turns of the helical conductor pattern with material of the first insulative layer.

14. A method for making a conductive assembly for a medical electrical lead, the method comprising:
   masking a non-conductive tubular core member by winding a mask helically around the non-conductive tubular core member to form gaps between adjacent turns of the mask;
   depositing a conductive layer on the mask and on the non-conductive tubular core member in the gaps between adjacent turns of the mask;
   removing the mask from the tubular core member such that portions of the conductive layer deposited on the mask are removed with the mask while a helical conductive pattern remains on the tubular core member, the helical conductive pattern comprising the conductive layer; and
   covering the tubular core member and the helical conductive pattern with a insulative layer.

15. The method of claim 14, wherein masking the tubular core member comprises spinning a fibrous material over the tubular core member.

16. The method of claim 14, wherein the conductive layer is deposited on the masked tube via plasma enhanced chemical vapor deposition (PECVD).

17. The method of claim 14, wherein the tubular core member is covered with the insulative layer via any of spray coating, dip coating, pulsed laser deposition, or condensation.

18. The method of claim 14, wherein the tubular core member and the insulative layer are comprised of a polymer.

19. The method of claim 14, wherein masking the non-conductive tubular core member further comprises indenting the non-conductive tubular core member with the mask as the mask is helically wound around the non-conductive tubular core member.

20. The method of claim 14, wherein removal of the mask from around the tubular core member exposes spaces of the non-conductive tubular core member between adjacent turns of the helical conductor pattern.

21. The method of claim 20, wherein covering the tubular core member with the insulative layer comprises filling the spaces between adjacent turns of the helical conductor pattern with material of the insulative layer.

* * * * *